US011419714B2

(12) United States Patent
Schulick et al.

(10) Patent No.: US 11,419,714 B2
(45) Date of Patent: Aug. 23, 2022

(54) STENT AND METHOD OF STENTING AN ABDOMINAL AORTIC ANEURYSM

(71) Applicant: THE JOHNS HOPKINS UNIVERSITY, Baltimore, MD (US)

(72) Inventors: Andrew Schulick, Bethesda, MD (US); Devika Singh, Bethesda, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 16/623,077

(22) PCT Filed: Jun. 19, 2018

(86) PCT No.: PCT/US2018/038271
§ 371 (c)(1),
(2) Date: Dec. 16, 2019

(87) PCT Pub. No.: WO2018/236860
PCT Pub. Date: Dec. 27, 2018

(65) Prior Publication Data
US 2020/0179095 A1   Jun. 11, 2020

Related U.S. Application Data

(60) Provisional application No. 62/523,496, filed on Jun. 22, 2017.

(51) Int. Cl.
*A61F 2/07* (2013.01)
*A61F 2/856* (2013.01)
*A61F 2/06* (2013.01)

(52) U.S. Cl.
CPC ............ *A61F 2/07* (2013.01); *A61F 2/856* (2013.01); *A61F 2002/061* (2013.01); *A61F 2002/065* (2013.01)

(58) Field of Classification Search
CPC .......... A61F 2002/061; A61F 2002/065; A61F 2002/067; A61F 2/07; A61F 2002/072–2002/077; A61F 2/856
See application file for complete search history.

(56) References Cited

U.S. PATENT DOCUMENTS

2001/0004707 A1 * 6/2001 Dereume ............. A61F 2/954
  623/1.16
2002/0058993 A1 * 5/2002 Landau ................ A61F 2/86
  623/1.36

(Continued)

FOREIGN PATENT DOCUMENTS

WO   2007/107327 A1   9/2007
WO   2009/140638 A1   11/2009

OTHER PUBLICATIONS

Minion, David. "Molded parallel endografts for branch vessel preservation during endovascular aneurysm repair in challenging anatomy." International Journal of Angiology 21.02 (2012): 081-084.

(Continued)

*Primary Examiner* — Leslie Lopez
(74) *Attorney, Agent, or Firm* — Tarolli, Sundheim, Covell & Tummino LLP

(57) ABSTRACT

A stent includes a fluid-permeable stent body having longitudinally separated proximal and distal stent ends. The stent body has inner and outer stent body surfaces. The stent body defines at least one longitudinally extending primary lumen and at least two longitudinally extending secondary lumens laterally spaced from one another with at least a portion of the primary lumen interposed laterally therebetween. The secondary and primary lumens all are at least partially fluid-permeable between the inner and outer stent body surfaces. At least one fluid-impermeable and longitudinally extending berm is located directly laterally adjacent a cor- (Continued)

responding secondary lumen. The berm prevents fluid flow laterally between at least a portion of the corresponding secondary lumen and a space laterally opposite the secondary lumen beyond the berm. A method of using the stent in at least partially extending a superior landing zone of an abdominal aortic aneurysm is also described.

24 Claims, 5 Drawing Sheets

(56) References Cited

U.S. PATENT DOCUMENTS

2006/0074481 A1  4/2006  Vardi et al.
2013/0245745 A1  9/2013  Vong et al.

OTHER PUBLICATIONS

PCT International Search Report and Written Opinion for corresponding PCT Application Serial No. PCT/US2018/038271, dated Aug. 24, 2018, pp. 1-7.

\* cited by examiner

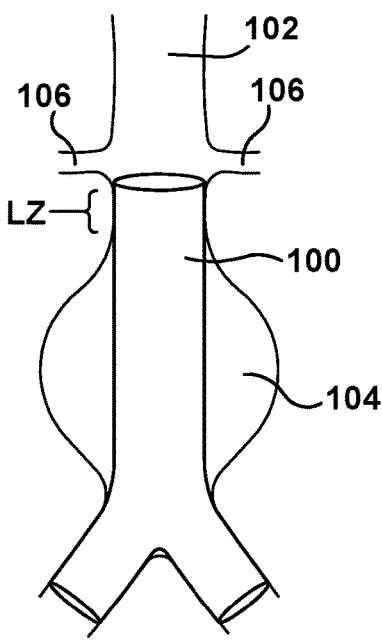
Fig. 1
(Prior Art)
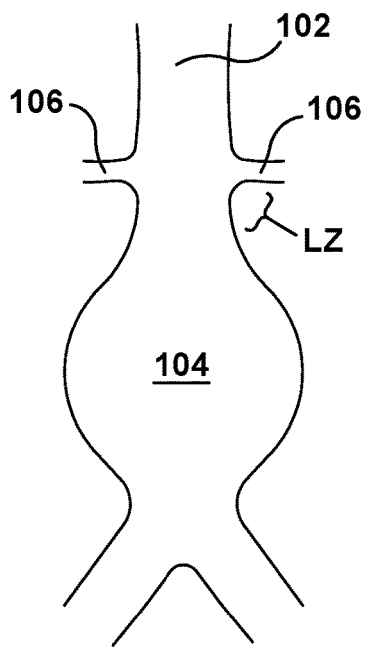
Fig. 2
(Prior Art)
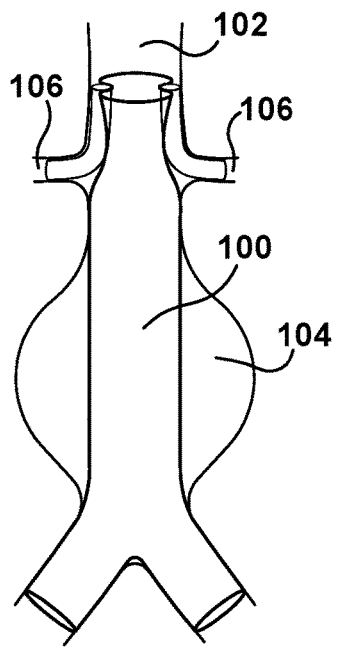
Fig. 3
(Prior Art)
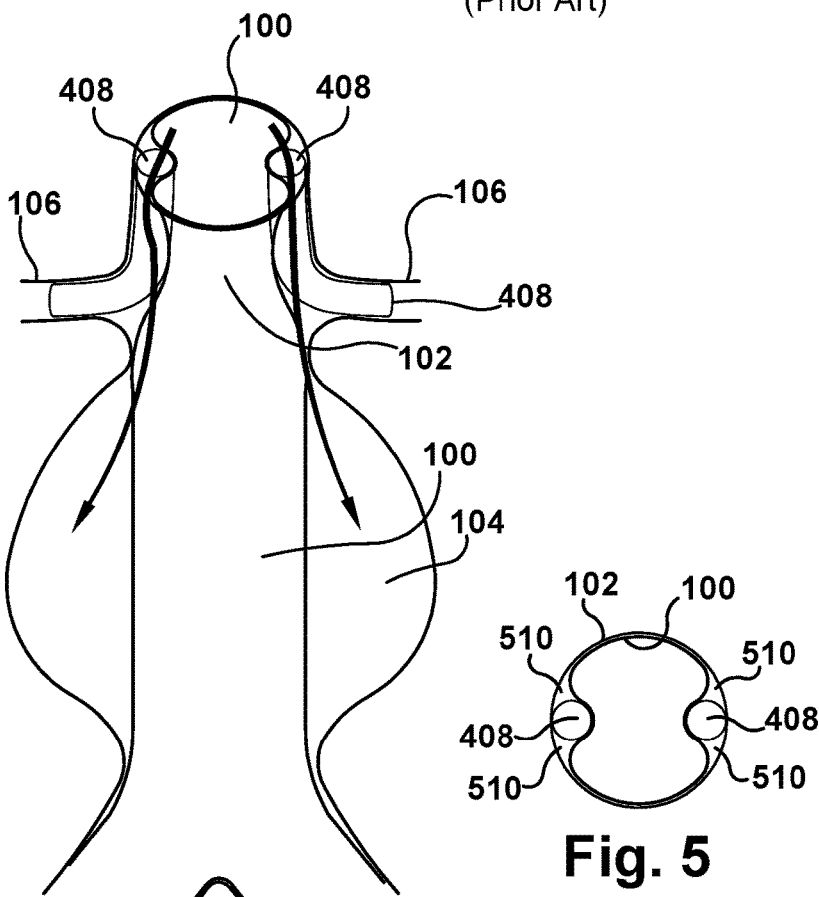
Fig. 4
(Prior Art)
Fig. 5
(Prior Art)

STENT AND METHOD OF STENTING AN ABDOMINAL AORTIC ANEURYSM

RELATED APPLICATION

This application claims priority from U.S. Provisional Application No. 62/523,496, filed 22 Jun. 2017, the subject matter of which is incorporated herein by reference in its entirety.

TECHNICAL FIELD

This disclosure relates to an apparatus and method for use of a stent and, more particularly, to a method and apparatus for stenting an abdominal aortic aneurysm.

BACKGROUND

Abdominal aortic aneurysms ("AAA") are a leading cause of death today. The most common AAA is the infra-renal variety, which is also generally the simplest to repair. Currently most can be repaired via the "minimally invasive" endovascular approach, in which a bifurcated, fabric-covered sleeve is introduced through the femoral arteries, relining the aorta with a smaller flow channel, and diverting blood away from the expanding aneurysm sac. This arrangement is shown in FIG. 1, with the bifurcated sleeve 100 being shown in the aorta 102 spanning the AAA 104.

Success of the AAA stenting procedure largely depends on having an adequate "landing zone" LZ between the renal arteries 106 and the top of the AAA 104 for the proximal end of the bifurcated sleeve 100 to seal against. In circumstances in which adequate landing zone LZ is not present (the anatomical situation shown in FIG. 2), other, more complicated techniques may be required to help seat the bifurcated sleeve 100 firmly against the aorta 102 without blocking the renal arteries 106.

A new technique to repair AAA in an aorta 102 having a relatively short landing zone LZ which is not amenable to conventional repair is to extend the proximal landing zone LZ by artificially "elevating" or extending the orifices of the renal arteries 106. This is done by placing fabric covered chimney grafts 408 into the renal arteries 106, as shown in FIGS. 3-5. These chimney grafts 408 extend proximally along the aorta 102, creating a new, longer, landing zone LZ in which to anchor the proximal end of the bifurcated sleeve 100. The issue with this so-called "chimney" technique remains the presence of gutters 510 (shown in top view in FIG. 5) that are inadvertently created when round objects are placed adjacent to each other in a round enclosure.

Because the adjacent walls of the chimney grafts 408 and bifurcated sleeve 100 do not conform perfectly to one another, tracks or gutters 510 run parallel to the chimney grafts 408. Blood flow can continue to enter the AAA 104 aneurysm sac (a phenomenon known as "endoleak") by seeping through the gutters 510 between the nonpermeable walls of the bifurcated sleeve 100 and the chimney grafts 408, which can cause unwanted continued aneurysm expansion.

The longer the chimney graft 408, and therefore the longer the gutter 510 associated with it, the less likely there is to be an endoleak between the bifurcated sleeve 100 and the chimney grafts 408, since blood has a further distance to travel and clotting may at least partially help to close off those gutters 510. However, there is a limit on the length of the chimney grafts 408: namely, the linear distance along the aorta 102, between the renal artery 106 orifices and the orifice for the superior mesenteric artery 612 ("SMA"; the next more proximal branch). This distance determines the maximum additional landing zone LZ that can be achieved using renal chimney grafts, without having to resort to additional chimney grafts 408 in the visceral vessels, such as the celiac artery 614 and SMA 612.

SUMMARY

In an aspect, a stent is described. A fluid-permeable tubular stent body includes longitudinally separated proximal and distal stent ends. The stent body has inner and outer stent body surfaces. The stent body defines at least one longitudinally extending primary lumen and at least two longitudinally extending secondary lumens laterally spaced from one another with at least a portion of the primary lumen interposed laterally therebetween. The secondary and primary lumens all are at least partially fluid-permeable between the inner and outer stent body surfaces. At least one fluid-impermeable and longitudinally extending berm is located directly laterally adjacent a corresponding secondary lumen. The berm prevents fluid flow laterally between at least a portion of the corresponding secondary lumen and a space laterally opposite the secondary lumen beyond the berm.

In an aspect, a method of stenting an abdominal aortic aneurysm ("AAA") is described. A landing zone stent is provided. The landing zone stent includes a fluid-permeable tubular stent body, including longitudinally separated proximal and distal stent ends. The stent body has inner and outer stent body surfaces. The stent body defines at least one longitudinally extending primary lumen and at least two longitudinally extending secondary lumens laterally spaced from one another with at least a portion of the primary lumen interposed laterally therebetween. The secondary and primary lumens all are at least partially fluid-permeable between the inner and outer stent body surfaces. At least one fluid-impermeable and longitudinally extending berm is located directly laterally adjacent a corresponding secondary lumen. The landing zone stent is placed in a target position superior to the abdominal aortic aneurysm with the distal stent end located superior to the renal arteries. Fluid flow is allowed laterally between the celiac and superior mesenteric arteries and the primary lumen through the stent body. At least one fluid-impermeable tubular chimney graft is provided. At least a proximal portion of the chimney graft is located within a corresponding secondary lumen. At least a distal portion of the chimney graft is located within a corresponding renal artery. Fluid flow between the renal artery and the corresponding secondary lumen is allowed through the chimney graft.

In an aspect, a stent-graft system for use in at least partially extending a superior landing zone of an abdominal aortic aneurysm ("AAA") is described. The stent-graft includes a stent for selective placement within an aorta. The stent includes a fluid-permeable tubular stent body, including longitudinally separated proximal and distal stent ends. The stent body has inner and outer stent body surfaces. The stent body defines at least one longitudinally extending primary lumen and at least two longitudinally extending secondary lumens laterally spaced from one another with at least a portion of the primary lumen interposed laterally therebetween. The secondary and primary lumens all are at least partially fluid-permeable between the inner and outer stent body surfaces. At least one fluid-impermeable and longitudinally extending berm is located directly laterally adjacent a corresponding secondary lumen. The berm prevents fluid flow laterally between at least a portion of the corresponding secondary lumen and a space laterally opposite the secondary lumen beyond the berm. At least one fluid-impermeable tubular chimney graft has longitudinally spaced proximal and distal chimney graft ends. The proximal chimney graft end is selectively located within a corresponding secondary lumen when the distal chimney graft end extends distally from the distal stent end.

BRIEF DESCRIPTION OF THE DRAWINGS

For a better understanding, reference may be made to the accompanying drawings, in which:

FIG. 1 is a schematic side view of a prior art device and use environment;

FIG. 2 is a schematic side view of a use environment;

FIG. 3 is a schematic side view of a prior art device and use environment;

FIG. 4 is a schematic top perspective view of the prior art device and use environment of FIG. 3;

FIG. 5 is a schematic top view of the prior art device and use environment of FIG. 3;

DESCRIPTION OF ASPECTS OF THE DISCLOSURE

Figure 6:
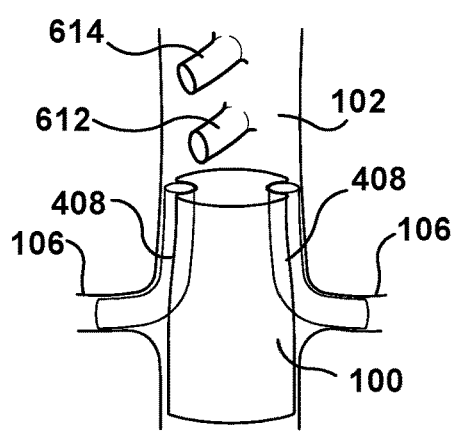
FIG. 6 is a schematic side view of a component of a prior art device in a use environment.

Unless defined otherwise, all technical and scientific terms used herein have the same meaning as is commonly understood by one of skill in the art to which the present disclosure pertains.

As used herein, the term "subject" can be used interchangeably with the term "patient" and refer to any warm-blooded organism including, but not limited to, human beings, pigs, rats, mice, dogs, goats, sheep, horses, monkeys, apes, rabbits, cattle, farm animals, livestock, etc.

As used herein, the terms "treat" or "treating" can refer to therapeutically regulating, preventing, improving, alleviating the symptoms of and/or reducing the effects of an abdominal aortic aneurysm ("AAA"). As such, treatment also includes situations where an AAA, or at least a symptom associated therewith, is completely inhibited, e.g., prevented from happening or stopped (e.g., terminated) such that the subject no longer suffers from the AAA, or at least the symptom(s) associated therewith.

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "directly adjacent" another feature may have portions that overlap or underlie the adjacent feature, whereas a structure or feature that is disposed "adjacent" another feature might not have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of a device in use or operation, in addition to the orientation depicted in the figures. For example, if a device in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

The invention comprises, consists of, or consists essentially of the following features, in any combination.

Figure 7:
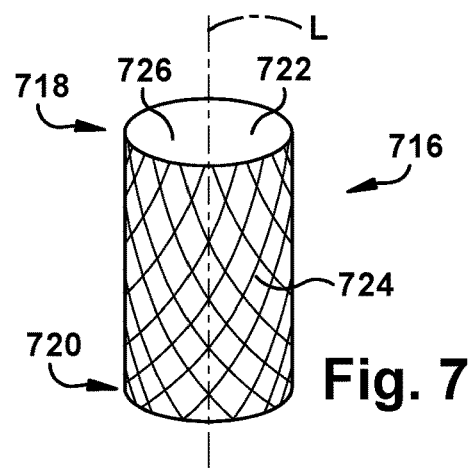
FIG. 7 is a schematic top perspective view of a component of an aspect of the present invention.

FIG. 7 depicts a fluid-permeable tubular stent body 716, including longitudinally separated proximal and distal stent ends 718 and 720, respectively. The stent body 716 has inner and outer stent body surfaces 722 and 724, respectively. The stent body 716 defines at least one longitudinally extending primary lumen 726. The longitudinal direction, as used herein, is substantially in the vertical direction, in the orientation of FIG. 7, and is parallel to the longitudinal axis L (shown in FIG. 7).

Figure 8:
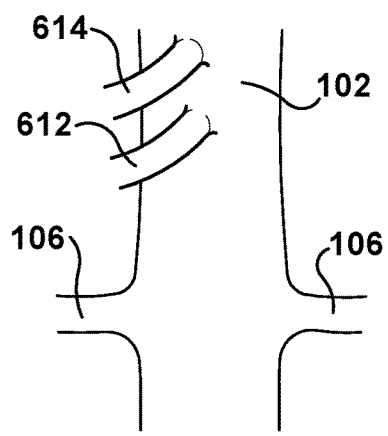
FIG. 8 is a schematic side view of a use environment.
Figure 9:
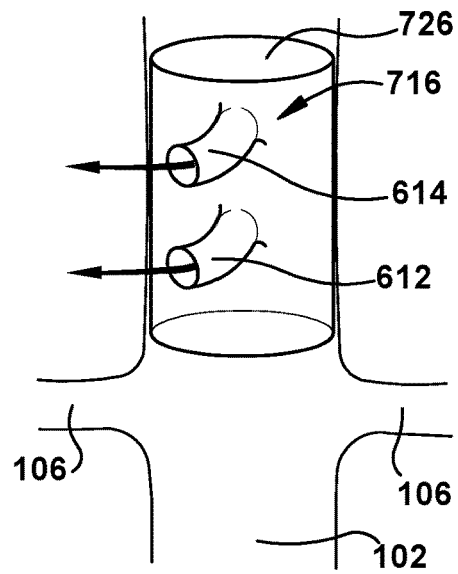
FIG. 9 is a schematic side view of the component of FIG. 7 in the use environment of FIG. 8.

FIG. 8 depicts a portion of an aorta 102, with the renal arteries 106, SMA 612, and celiac artery 614 shown. In FIG. 9, the tubular stent body 716 is shown in an example use position, superior to the renal arteries 106. As is shown in FIG. 9, the permeable nature of the stent body 716 permits fluid flow between the inner and outer stent body surfaces 722 and 724 and thus facilitates direct fluid communication between the primary lumen 726 and at least one of the SMA 612 and the celiac artery 614. The term "permeable" is used herein to indicate that a structure has pores or openings that permit fluids to pass through. For example, the stent body 716 could at least partially be made of an open-cell weave of any material (including fabric and metal), with the cells being configured to allow fluid particles of a desired size (e.g., blood cells) to pass through.

Figure 10:
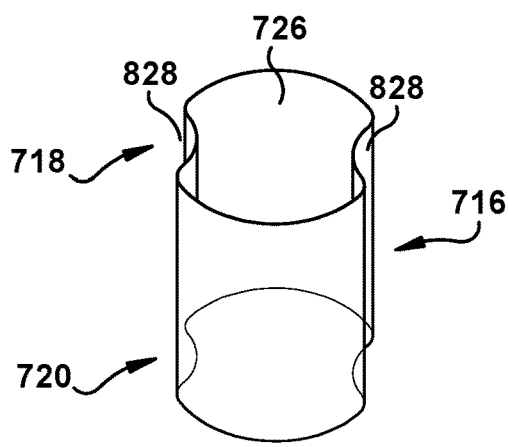
FIG. 10 is a schematic top perspective view of components of the aspect of FIG. 7.
Figure 11:
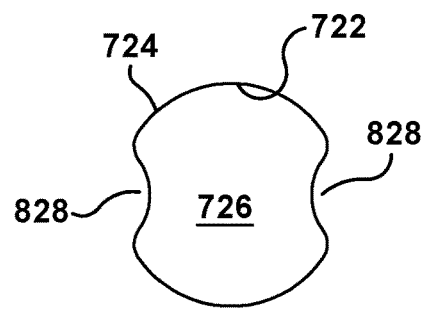
FIG. 11 is a schematic top view of the components of FIG. 10.

As shown in FIGS. 10-11, the stent body 716 can also include at least two longitudinally extending secondary lumens 828 laterally spaced from one another with at least a portion of the primary lumen 726 interposed laterally therebetween. The term "lateral" is used herein to reference a direction substantially within a plane which is substantially perpendicular to the longitudinal direction. The secondary lumens 828 can be formed in any desired manner, including by the provision of "sheets" of material attached to the inner stent body surface 722 at the secondary lumen 828 positions, the local separation of layers of a multi-layer stent body 716, the attachment of tubes of permeable material to the inner stent body surface 722, or in any other desired manner.

As shown in FIGS. 10-11, two secondary lumens 828 may be diametrically opposed from one another across the stent body 716—that is, they may be located on opposite ends of a diameter substantially bifurcating the stent body 716. Any number of secondary lumens 828 may be provided, in any desired positions around the circumference of the stent body 716, as desired for a particular use environment of the present invention, however.

The secondary and primary lumens 726 and 828 are all at least partially fluid-permeable between the inner and outer stent body surfaces 722. For example, a supermajority (i.e., a majority—such as, but not limited to, two-thirds or three-fifths—which is greater than a simple majority) of a lateral perimeter of the primary lumen 722 may be fluid-permeable to an ambient space outside the stent. As another example, at least half of a lateral perimeter of each secondary lumen 828 may be fluid-permeable to an ambient space outside the stent. In an additional example, up to half of a lateral perimeter of each secondary lumen 828 may be fluid-permeable to an ambient space outside the stent. As used herein, the term "lateral perimeter" indicates a boundary or outline of a structure within a lateral plane, as taken at any longitudinal position along the length of that structure. Optionally, and as shown in FIG. 10, the stent body 716 may have a substantially constant lateral perimeter at all longitudinal positions along the length of the stent body 716.

Figure 12:
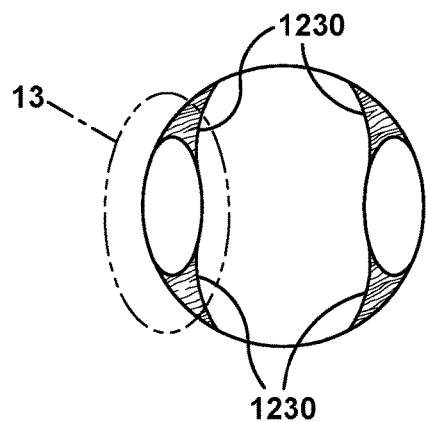
FIG. 12 is a schematic top view of components of the aspect of FIG. 10.

Turning to FIG. 12, at least one substantially fluid-impermeable and longitudinally extending berm 1230 (four shown) may be located directly laterally adjacent a corresponding secondary lumen 828. The term "fluid-impermeable" here does not require absolute fluid-tightness; it is contemplated that some de minimis amount of fluid could leak through and/or around the berms 1230, but that such small amount of fluid penetration would not be significant in the use environment of the stent.

The berm(s) 1230 may prevent fluid flow laterally between at least a portion of the corresponding secondary lumen 828 and a space laterally opposite the secondary lumen 828 beyond the berm 1230. Examples of spaces "laterally opposite the secondary lumen 828 beyond the berm 1230" include the primary lumen 726, another secondary lumen 828, and the ambient space around the stent.

Figure 13:
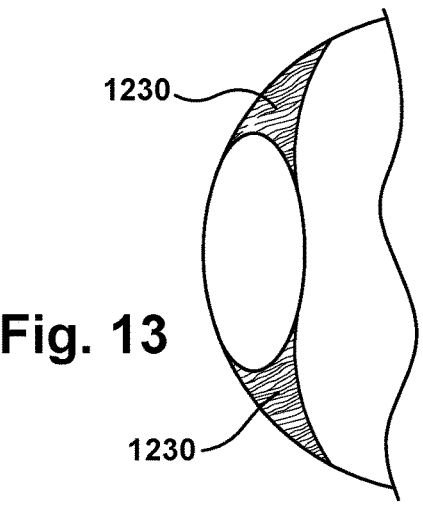
FIG. 13 is a detail view of area 13 of FIG. 12.

Optionally, and as shown in FIGS. 12-13, each secondary lumen 828 could be associated with two berms 1230, the two berms 1230 being spaced laterally apart from each other by at least a portion of the corresponding secondary lumen 828.

Also as shown in FIGS. 12-13, the berm(s) 1230 can laterally fillet the longitudinally-oriented interface between the primary and secondary lumens, and thus smooth the transition between that interface. The term "fillet" is used here to mean "give a rounded appearance to a concave junction formed where two surfaces meet (as at an angle)".

Figure 14:
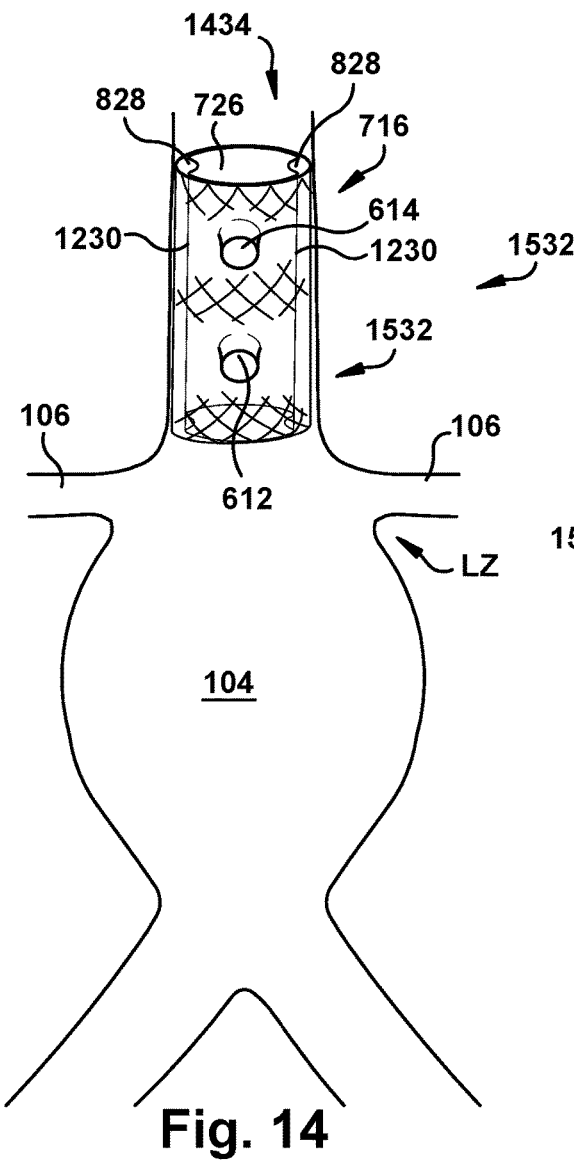
FIGS. 14-16 schematically depict an example sequence of operation of an aspect of the present invention.
Figure 15:
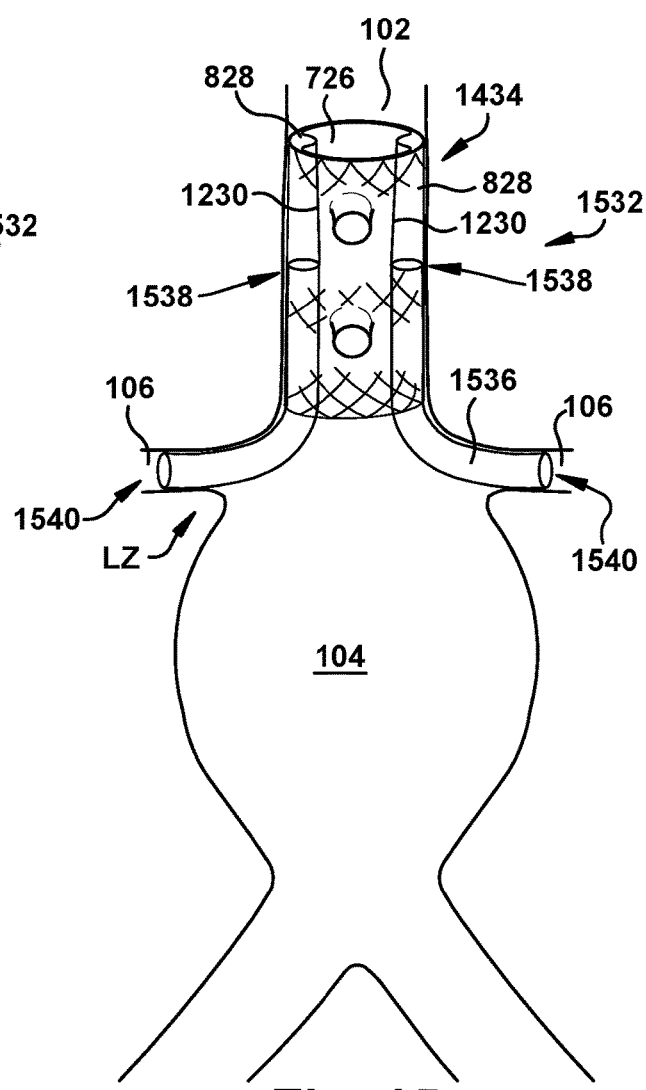

As shown in FIGS. 14-15, an aspect of the present invention may include a stent-graft system 1532 for use in at least partially extending a superior landing zone LZ of an AAA 104. The stent-graft system 1532 includes a stent 1434 (which can be considered a "landing zone stent") for selective placement within an aorta 102. The stent 1434 includes a stent boy 716 having primary and secondary lumens 726 and 828 and berms 1230, as described above.

Figure 16:
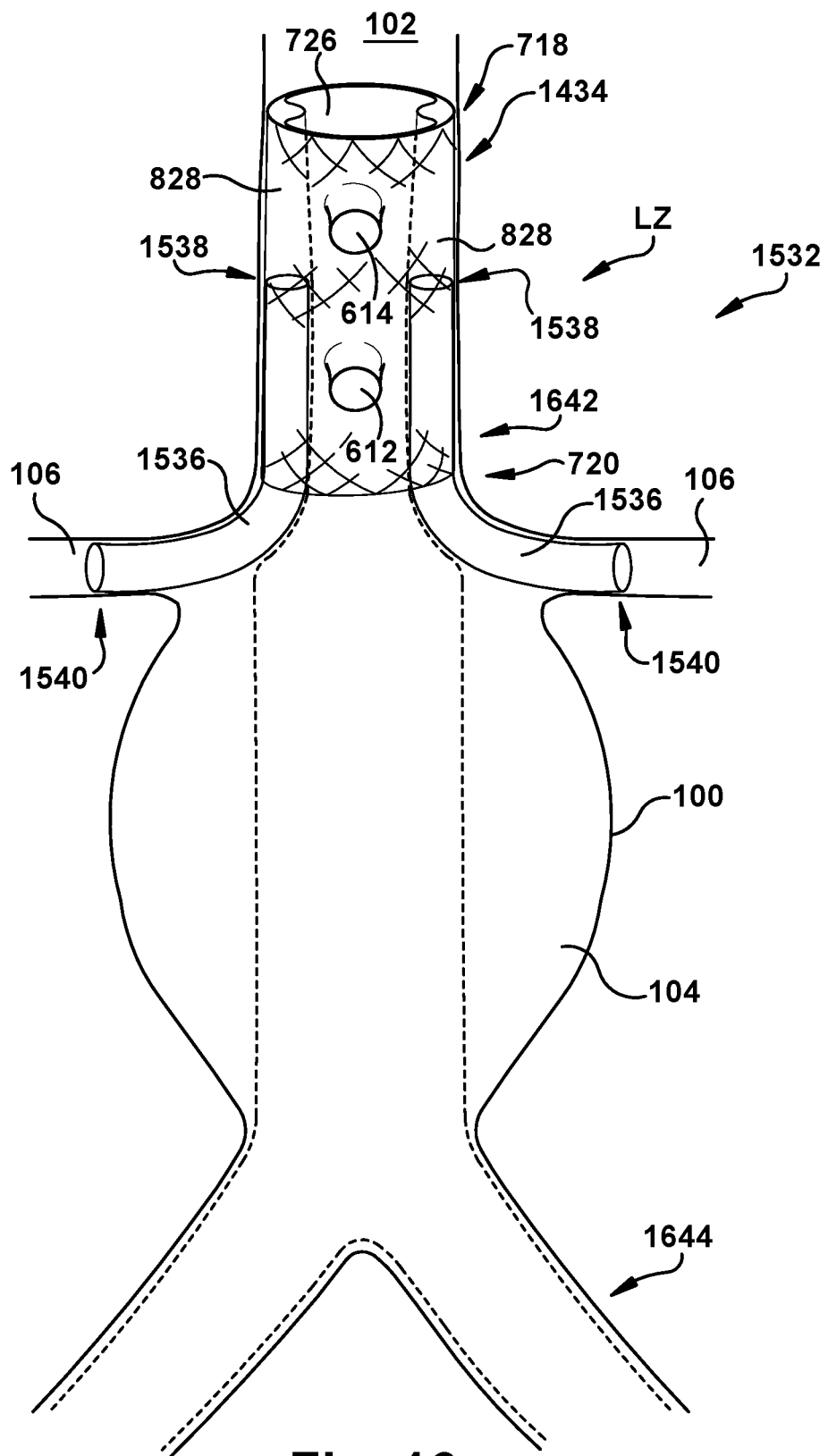

With reference to FIG. 15, the stent-graft system 1532 may also include at least one fluid-impermeable tubular chimney graft 1536 (two shown) having longitudinally spaced proximal and distal chimney graft ends 1538 and 1540, respectively. The proximal chimney graft end 1538 is selectively located within a corresponding secondary lumen 828, as shown in FIGS. 15-16, when the distal chimney graft end 1540 extends distally from the distal stent end 720. Stated differently, the chimney grafts 1536 may "hang down from" the stent body 716 when installed in the secondary lumens 828 as part of the stent-graft system 1532. The chimney graft 1536 may be held in the secondary lumen 828 in any desired manner, and need not be actually secured to the stent body 716.

The stent-graft system 1532 may include an AAA stent-graft (i.e., a bifurcated sleeve 100) having longitudinally opposed proximal and distal AAA stent-graft ends 1642 and 1644, as shown in dashed line in FIG. 16. In the stent-graft system 1532 as installed, the AAA stent-graft 100 selectively longitudinally spans the AAA 104 with the proximal and distal AAA stent-graft ends 1642 and 1644 being anchored proximally and distally of the AAA 104, respectively, within the aorta 102. Optionally, and as shown in FIG. 16, the proximal AAA stent-graft end 1642 may be maintained within the primary lumen 726 of the stent 1434 when the AAA stent-graft 100 longitudinally spans the AAA 104.

For many AAA 104 patients, the combination of the AAA stent-graft 100 and the primary lumen 726 of the stent 1434 provides for bloodflow through the aorta 102 while preventing bloodflow between the outer stent body surface 724 and the aorta 102 which could lead to an endoleak. Concurrently, the chimney grafts 1530 operate in a "chimney" or "snorkel" type manner to provide fluid communication between the renal arteries 106 and the aorta 102 superior to the AAA 104, while the berms 1230 substantially prevent blood from leaking through the "gutters" between the primary and secondary lumens 726 and 828 and thus obtaining fluid access to the AAA 104 past the outer stent body surface 724.

The sequence of FIGS. 14-16 depicts a method of stenting an AAA 104. A stent 1434 is placed in a target position superior to the AAA 104 with the distal stent end 720 located superior to the renal arteries 106. Fluid flow is allowed laterally between the celiac and superior mesenteric arteries 614 and 612 and the primary lumen 726 directly through the permeable stent body 716. This is the configuration shown in FIG. 14.

At least one fluid-impermeable tubular chimney graft 1536 is provided, with at least a proximal portion of the chimney graft 1536 (e.g., the proximal chimney graft end 1538) being located within a corresponding secondary lumen 828. At least a distal portion of the chimney graft 1536 (e.g., the distal chimney graft end 1540) is located within a corresponding renal artery 106. Fluid flow is allowed between the renal artery 106 and the corresponding secondary lumen 828 through the chimney graft 1536, as shown in FIG. 15.

With reference to FIG. 16, an AAA stent-graft 100 having longitudinally opposed proximal and distal AAA stent-graft ends 1642 and 1644 is provided. The AAA 104 is longitudinally spanned with the AAA stent-graft 100, with the proximal and distal AAA stent-graft ends 1642 and 1644 being anchored proximally and distally of the AAA 100, respectively, within the aorta 102. For example, the proximal AAA stent-graft end 1642 could be maintained (via frictional fit, one or more fasteners, adhesive, or any other desired affixation scheme) within the primary lumen 726 of the stent 1434. With the berm(s) 1230, fluid flow is prevented laterally between at least a portion of the corresponding secondary lumen 828 and a space laterally opposite the secondary lumen 828 beyond the berm 1230 (e.g., the primary lumen 726, another secondary lumen 828, and the ambient space around the stent).

Figure 17A:
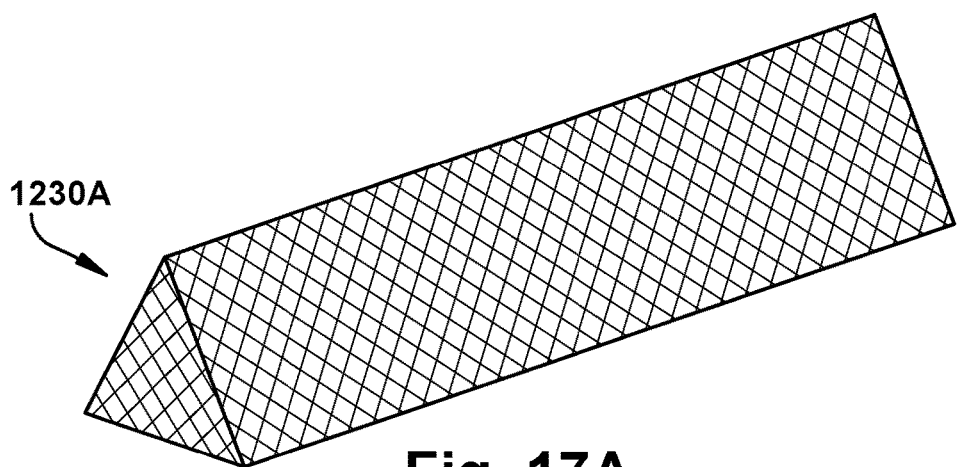
FIGS. 17A-17C schematically depict example use configurations for a component of an aspect of the present invention.
Figure 17B:
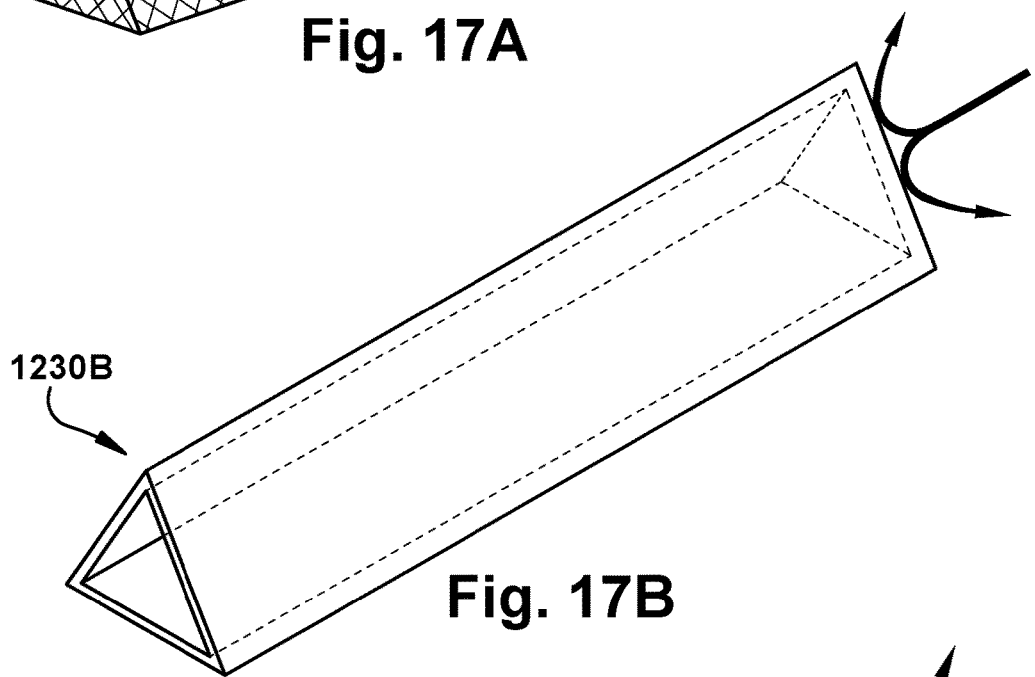
Figure 17C:
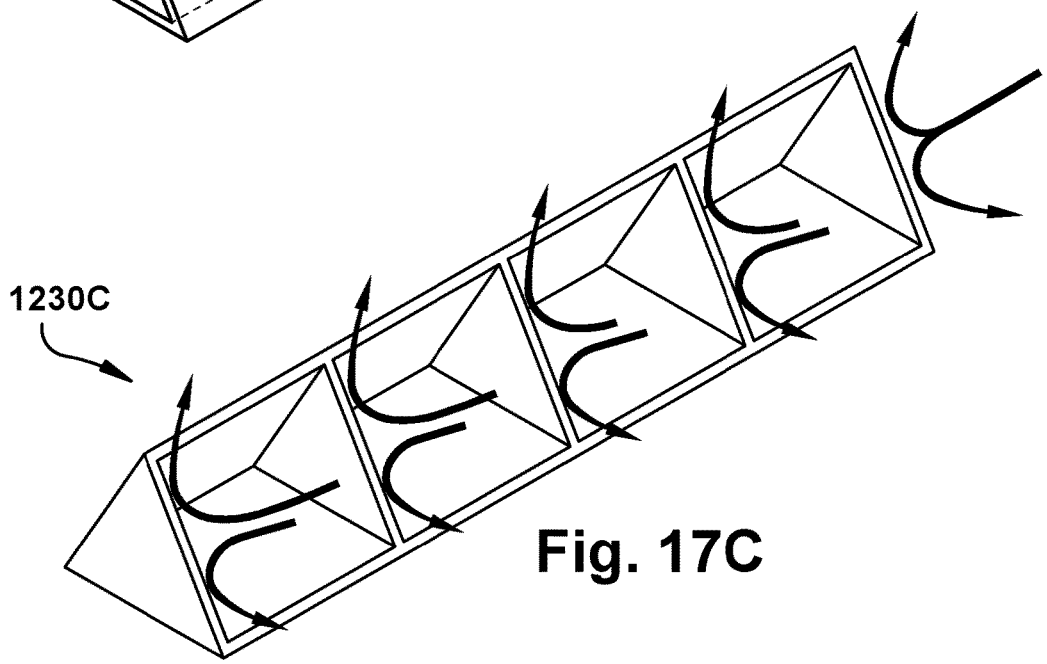

FIGS. 17A-17C schematically depict examples of berms 1230 which could be used as desired, singly or in combination, in a stent-graft system 1532. The berm 1230A of FIG. 17A is a solid, single-piece construct (e.g., a foam prism shape, which may be covered with impermeable fabric)—however, this solidity may impair compressibility of the berm 1230A for packing in an introducer sheath. The berm 1230B of FIG. 17B is a hollow prism-shaped structure, which may be configured with one or more "endcaps" or apical caps to prevent fluid flow longitudinally therethrough—this berm 1230B may be slightly more compressible than the berm 1230A of FIG. 17A. The berm 1230C of FIG. 17C has an open wire framed prism structure, with one or more thin flow-occluding flaps ("flow stops") extending laterally therein. A series of flaps may be provided to the berm 1230C of FIG. 17C, to provide the user with flexibility regarding the longitudinal placement of the chimney graft 408 in the secondary lumen 828 while still substantially blocking bloodflow therethrough.

Regardless of the specific configuration, though, the three longitudinal sides of each berm 1230 may be substantially covered by the aorta 102, the primary lumen 726, and the secondary lumen 828. Thus, the lateral cross-section of the berm 1230 is the remaining surface to be covered to prevent fluid flow through the berm 1230. Any of the berms 1230A, 1230B, 1230C, or any other desired design or combination of designs may be used with a particular stent-graft system 1532. One of ordinary skill in the art can readily configure a berm 1230 design for any desired reason, including considering the ability of the berm 1230 to be constrained in a delivery device. For example, the berm 1230C of FIG. 17C might be suited for delivery in a lower-profile sheath than would the berms 1230A or 1230B of FIGS. 17A-B.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. A "predetermined" status may be determined at any time before the structures being manipulated actually reach that status, the "predetermination" being made as late as immediately before the structure achieves the predetermined status. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

We claim:

1. A stent, comprising:
    a fluid-permeable tubular stent body, including longitudinally separated proximal and distal stent ends, the stent body having inner and outer stent body surfaces, the stent body defining at least one longitudinally extending primary lumen and at least two longitudinally extending secondary lumens laterally spaced from one another with at least a portion of the primary lumen interposed laterally therebetween, the secondary and the primary lumens all being at least partially fluid-permeable between the inner and the outer stent body surfaces, in a direction extending laterally through the inner and the outer stent body surfaces;
    at least one fluid-impermeable and longitudinally extending berm located directly laterally adjacent a corresponding one of the at least two secondary lumens, the berm preventing fluid flow laterally between at least a portion of the corresponding one of the at least two secondary lumens and a space laterally opposite the corresponding secondary lumen beyond the berm.

2. The stent of claim 1, wherein the at least two secondary lumens are diametrically opposed from one another across the stent body.

3. The stent of claim 1, wherein each of the at least two secondary lumens is associated with two berms, the two berms being spaced laterally apart from each other by at least a portion of the secondary lumen with which the two berms are associated.

4. The stent of claim 3, wherein the two berms associated with a first one of the at least two secondary lumens are each spaced laterally apart within the primary lumen from the two berms associated with a second one of the at least two secondary lumens.

5. The stent of claim 1, wherein a supermajority of a lateral perimeter of the primary lumen is fluid-permeable to an ambient space outside the stent.

6. The stent of claim 1, wherein at least half of a lateral perimeter of each secondary lumen is fluid-permeable to an ambient space outside the stent.

7. The stent of claim 1, wherein up to half of a lateral perimeter of each secondary lumen is fluid-permeable to an ambient space outside the stent.

8. The stent of claim 1, wherein the berm laterally fillets a longitudinally-oriented interface between the primary and the secondary lumens.

9. The stent of claim 1, wherein the at least one berm has an open wire framed prism structure, with one or more thin flow-occluding flaps extending laterally therein.

10. The stent of claim 1, wherein the longitudinally separated proximal and distal stent ends are concurrently placed in mutual fluid communication via each of the primary lumen and the at least two secondary lumens.

11. The stent of claim 1, wherein the at least two longitudinally extending secondary lumens laterally spaced from one another with at least a portion of the primary lumen interposed laterally therebetween along an entire longitudinal extent of the stent body.

12. A method of stenting an abdominal aortic aneurysm (AAA), the method comprising:
provinding a landing zone stent, including
a fluid-permeable tubular stent body, including longitudinally separated proximal and distal stent ends, the stent body having inner and outer stent body surfaces, the stent body defining at least one longitudinally extending primary lumen and at least two longitudinally extending secondary lumens laterally spaced from one another with at least a portion of the primary lumen interposed laterally therebetween, the secondary and the primary lumens all being at least partially fluid-permeable between the inner and the outer stent body surfaces, in a direction extending laterally through the inner and the outer stent body surfaces, and
at least one fluid-impermeable and longitudinally extending berm located directly laterally adjacent a corresponding one of the at least two secondary lumens;
placing the landing zone stent in a target position superior to the abdominal aortic aneurysm with the distal stent end located superior to renal arteries;
allowing fluid flow laterally between a celiac and a superior mesenteric arteries and the primary lumen through the stent body;
providing at least one fluid-impermeable tubular chimney graft;
locating at least a proximal portion of the chimney graft within a corresponding one of the secondary lumens;
locating at least a distal portion of the chimney graft within a corresponding renal artery; and
allowing fluid flow between the corresponding renal artery and the corresponding secondary lumen through the chimney graft.

13. The method of claim 12, including:
providing the AAA stent-graft having longitudinally opposed proximal and distal AAA stent-graft ends; and
longitudinally spanning the AAA with the AAA stent-graft, the proximal and the distal AAA stent-graft ends being anchored proximally and distally of the AAA, respectively, within an aorta.

14. The method of claim 13, wherein the longitudinally spanning the AAA with the AAA stent-graft, the proximal and the distal AAA stent-graft ends being anchored proximally and distally of the AAA, respectively, within the aorta includes maintaining the proximal AAA stent-graft end within the primary lumen of the landing zone stent.

15. The method of claim 12, including, with the berm, preventing fluid flow laterally between at least a portion of the corresponding secondary lumen and a space laterally opposite the secondary lumen beyond the berm.

16. A stent-graft system for use in at least partially extending a superior landing zone of an abdominal aortic aneurysm (AAA), the stent-graft comprising:
a stent for selective placement within an aorta, the stent including
a fluid-permeable tubular stent body, including longitudinally separated proximal and distal stent ends, the stent body having inner and outer stent body surfaces, the stent body defining at least one longitudinally extending primary lumen and at least two longitudinally extending secondary lumens laterally spaced from one another with at least a portion of the primary lumen interposed laterally therebetween, the secondary and the primary lumens all being at least partially fluid-permeable between the inner and the outer stent body surfaces, in a direction extending laterally through the inner and the outer stent body surfaces, and
at least one fluid-impermeable and longitudinally extending berm located directly laterally adjacent a corresponding one of the at least two secondary lumens, the berm preventing fluid flow laterally between at least a portion of the corresponding secondary lumen and a space laterally opposite the secondary lumen beyond the berm; and
at least one fluid-impermeable tubular chimney graft having longitudinally spaced proximal and distal chimney graft ends, the proximal chimney graft end being selectively located within a corresponding one of the secondary lumens when the distal chimney graft end extends distally from the distal stent end.

17. The stent-graft system of claim 16, wherein the at least two secondary lumens are diametrically opposed from one another across the stent body.

18. The stent-graft system of claim 16, wherein each of the at least two secondary lumens is associated with two berms, the two berms being spaced laterally apart from each other by at least a portion of the secondary lumen associated with the two berms.

19. The stent-graft system of claim 16, wherein a supermajority of a lateral perimeter of the primary lumen is fluid-permeable to an ambient space outside the stent.

20. The stent-graft system of claim 16, wherein at least half of a lateral perimeter of each secondary lumen is fluid-permeable to an ambient space outside the stent.

21. The stent-graft system of claim 16, wherein up to half of a lateral perimeter of each secondary lumen is fluid-permeable to an ambient space outside the stent.

22. The stent-graft system of claim 16, wherein the berm laterally fillets a longitudinally-oriented interface between the primary and the secondary lumens.

23. The stent-graft system of claim 16, including an AAA stent-graft having longitudinally opposed proximal and distal AAA stent-graft ends, the AAA stent-graft selectively longitudinally spanning the AAA with the proximal and the distal AAA stent-graft ends being anchored proximally and distally of the AAA, respectively, within the aorta.

24. The stent-graft system of claim 23, wherein the proximal AAA stent-graft end is maintained within the primary lumen of the stent when the AAA stent-graft longitudinally spans the AAA.

\* \* \* \* \*